(12) United States Patent
Deecki

(10) Patent No.: US 6,532,971 B2
(45) Date of Patent: Mar. 18, 2003

(54) SANITARY POUCH WASHER

(76) Inventor: Robert George Deecki, 114 Delaware St., Archbald, PA (US) 18403

(*) Notice: Subject to any disclaimer, the term of this patent is extended or adjusted under 35 U.S.C. 154(b) by 0 days.

(21) Appl. No.: 10/123,238

(22) Filed: Apr. 17, 2002

(65) Prior Publication Data
US 2003/0034055 A1 Feb. 20, 2003

Related U.S. Application Data
(60) Provisional application No. 60/313,351, filed on Aug. 20, 2001.

(51) Int. Cl.⁷ .............................. B08B 3/02; B08B 9/00; A61F 5/442
(52) U.S. Cl. .............................. 134/22.18; 134/169 R; 134/170; 134/182; 604/277; 604/333; 604/334
(58) Field of Search .............................. 134/22.1, 22.18, 134/22.19, 24, 169 R, 170, 182; 604/277, 332, 334, 335, 333

(56) References Cited

U.S. PATENT DOCUMENTS

| | | | |
|---|---|---|---|
| 3,421,527 A | * 1/1969 | Dettman | 134/138 |
| 4,194,506 A | * 3/1980 | Voorhies | 604/334 |
| 4,941,878 A | 7/1990 | Petrik | |
| 5,037,408 A | * 8/1991 | Henry | 604/332 |
| 5,042,516 A | * 8/1991 | Chaney | 134/169 R |
| 5,709,236 A | 1/1998 | Rodriguez | |
| 5,738,668 A | 4/1998 | Bugajski | |
| 6,007,525 A | 12/1999 | Martell | |
| 6,224,581 B1 | * 5/2001 | Withers et al. | 604/334 |

* cited by examiner

Primary Examiner—Frankie L. Stinson
Assistant Examiner—Saeed Chaudhry
(74) Attorney, Agent, or Firm—Bacon & Thomas (57) ABSTRACT

A device for cleaning the interior and exterior of a colostomy pouch or the like. The device includes a middle water sprayer for cleaning the interior of the pouch and two lateral water sprayers for cleaning the exterior of the pouch. The water sprayers are attached to a conduit which is connected to a source of water such as a flexible hose connected to a faucet. A water shield is provided to prevent the operator from being sprayed during the cleaning procedure. The waste material cleaned from the pouch is discharged through the spray shield into a conventional toilet where the water and waste is removed by flushing the toilet.

22 Claims, 5 Drawing Sheets

SANITARY POUCH WASHER

This application claims the benefit of provisional application No. 60/313,351 filed on Aug. 20, 2001.

BACKGROUND OF THE INVENTION

1. Field of the Invention

The present invention pertains to the cleaning of colostomy pouches or bags and related bags which become contaminated with waste. More particularly, this invention relates to a device for cleaning such bags or pouches and a method for cleaning such bags or pouches, particularly a colostomy bag or pouch.

2. Background Information

Certain diseases and physical conditions require surgical intervention which involves the creation of an opening or orifice in the patient's body for the elimination of human waste therefrom. The waste, such as fecal material exits through the surgically created orifice or opening. Since the opening for the elimination of waste has been surgically created, the patient does not have any muscular control which could be used to effectively open and close the opening. Therefore, the patient is forced to wear a waste collection bag or pouch which is adapted to receive the waste from the opening in a sanitary manner so that the waste can be collected in the bag without leakage therefrom. Periodically, the bag must be detached from the opening so that the waste contents can be eliminated. It is therefore necessary to periodically clean the bag before it is used again. Typical surgical procedures which result in the creation of an orifice in the body for waste elimination include colostomy, surgical procedures, ileostomy surgical procedures and the like. These surgical procedures are generally referred to as ostomies and the waste collection containers are generally called ostomy pouches. Thus, for example, the pouch used by a colostomy patient is typically referred to as a colostomy pouch.

The opening created during colostomy surgery is an opening where a portion of the intestine, usually the large intestine or the colon empties fecal material through the opening. Such an opening is referred to as a stoma.

The colostomy pouch is configured to receive the fecal waste which passes through the stoma for sanitary collection therein. Typical colostomy pouches include an opening along an upper side portion thereof for connection to the stoma. The bottom of the pouch typically includes a generally cylindrical aperture which is used to empty the pouch.

The ostomy pouches are generally made of durable high grade rubber or plastic and are therefore generally not disposable. Thus, the accumulated waste must be periodically removed from the pouch in a cleaning procedure so that the pouch can be reused. Numerous types of cleaning devices are known in the art for cleaning colostomy pouches and the like. For example, U.S. Pat. No. 5,709,236 describes a colostomy pouch rinsing device which utilizes a spray head attached to a tube. Water is supplied to the tube through a rubber hose which is connected to a faucet. A water control handle is provided which allows the user to control the flow of water to the spray head. In operation, the spray head must be manually inserted into the colostomy pouch while the user holds the pouch over a toilet. Obviously, the user must manually hold the bag during the washing procedure which is not entirely satisfactory. In addition, it is easy for sprayed water to contact the user during the spraying procedure and the water and waste material exiting through the lower portion of the bag is prone to splashing in the toilet and can therefor contact the user.

The ostomy pouch flusher described in U.S. Pat. No. 4,941,878 uses a wand or tube which is inserted into the colostomy pouch so that water can be sprayed into the interior portion of the pouch during the cleaning operation. This device suffers from the same disadvantages described above.

U.S. Pat. No. 5,738,668 also describes a colostomy bag cleaning device which requires manually holding the bag and inserting a spray tube therein. This device, like the devices described above, requires the patient to manually insert the spray tube into the colostomy pouch while holding the pouch over the toilet. Thus, this device suffers from the same disadvantages noted above.

None of the prior art devices provide a simple and efficient cleaning operation wherein the user does not have to physically contact the colostomy bag during the cleaning procedure. In addition, none of the prior art devices provide for the simultaneous interior and exterior cleaning of the pouch. Furthermore, none of the prior art devices provide any means for protecting the user from spray and splashing during the cleaning process and none of the prior art devices provide any means for delivering water and waste from the cleaning process directly into the toilet in a sanitary manner.

In view of the above, it will be appreciated that there exists a need for an improved colostomy pouch cleaning apparatus which overcomes the disadvantages of the prior art devices, particularly the disadvantages noted above.

SUMMARY OF THE INVENTION

It is an objective of the present invention to provide a device for cleaning colostomy bags and the like which avoids the above noted disadvantages associated with the prior art devices.

It is also an objective of the present invention to provide a device for cleaning a colostomy bag or the like which allows sanitary cleaning of the bag without requiring the user to contact the bag during the cleaning operation.

It is also an objective of the present invention to provide a device for cleaning a colostomy bag or the like with sprayed water while protecting the user from spray and contaminated water during the cleaning procedure.

It is also an objective of the present invention to provide a cleaning device for cleaning colostomy bags and the like which provides for the safe and effective cleaning of both the interior and exterior portions of the bag, preferably, the simultaneous cleaning of the exterior and interior portions of the bag.

It is also an objective of the present invention to provide a cleaning device for cleaning a colostomy bag or the like which further provides for the delivery of waste and water from the cleaning procedure directly to a toilet bowl while protecting the user from contact with the waste and the water.

These and other objectives are obtained by providing a cleaning device which includes at least three water sprayers attached to a conduit for the supply of water thereto. One of the water sprayers is a middle water sprayer configured for receiving the pouch around the sprayer so that the middle water sprayer extends inside the pouch for cleaning the interior of the pouch with sprayed water. The other two sprayers are lateral water sprayers located alongside the middle water sprayer. The lateral water sprayers are configured to clean the exterior of the pouch when the middle water sprayer extends inside the pouch. Preferably, the three water sprayers operate simultaneously for effective cleaning action. A holder is provided for holding the pouch at a location wherein the middle sprayer is extended within the pouch for interior cleaning thereof and the lateral water sprayers are disposed alongside the exterior of the pouch for exterior cleaning thereof.

The device includes a conduit for passing water therethrough to thereby provide water for the water sprayers. The conduit is therefore in fluid communication with the sprayers so that water flowing through the conduit enters the sprayers and is thereby sprayed onto the pouch.

A coupler is advantageously employed for connecting the conduit to a source of water. The source of water should be pressurized so that a spray is formed when the water exits openings in the water sprayers. Conventional couplers are advantageously used so that the conduit can be readily connected to a flexible hose or to a standard faucet fixture, especially a hot water fixture to enhance the cleaning action of the water. The water should not be too hot. In particular, water which is scalding hot and which would burn an individuals skin should be avoided.

A dispenser may be connected to the conduit for dispensing a cleaning agent into the conduit for mixture with the water. Suitable cleaning agents include conventional soap and detergent. In addition, sanitizing agent or deodorizing agent may also be dispensed into the conduit through the dispenser for mixing with the water to thereby provide a sanitizing or deodorizing benefit.

A spray shield which is preferably cylindrical in shape with openings at the top and bottom thereof is advantageously used to shield the user from spray and water contaminated with human waste. In addition, the spray shield is used to direct the waste and water from the spray into a conventional toilet for disposal by flushing. This is accomplished by inserting the sprayers into the spray shield and introducing a bottom portion of the spray shield into the toilet so that water sprayed from the sprayers and the material cleaned from the pouch are directed through the spray shield to an opening in the bottom portion thereof which allows the water and waste to enter the toilet bowl for disposal by flushing.

The spray shield may advantageously contain a slot in an upper portion thereof to facilitate insertion of the sprayers therein.

The holder allows the cleaning operation to take place without the user having to touch the pouch. Preferably, the holder is a hanger made out of wire with a handle portion extending upwardly. The device may include a support for holding the hanger in the proper location and in a preferred embodiment, the support comprises a portion of the conduit. The hanger is advantageously configured so that when it is in contact with the support, the user can manually change the position of the pouch such as by lifting the hanger upward and/or laterally to aid in the cleaning operation.

The dispenser may be a pipe in fluid communication with the conduit. A valve is advantageously included in the pipe and the pipe is oriented for gravity feed into the conduit. In operation, the valve is opened to allow the introduction of cleaning agent, sanitizing agent or deodorizing agent or any combination thereof into the conduit for mixing with the water. Once these materials have been added to the conduit, the valve is closed so that pressurized water entering the device does not escape through the dispenser.

DETAILED DESCRIPTION OF THE INVENTION AND PREFERRED EMBODIMENTS

In a preferred embodiment the tube which forms the dispenser is oriented so that when the device is inserted into the spray shield in position for washing the pouch, the tube is oriented so that material inserted into an opening at the top of the tube is gravity fed into the conduit. Also, in this preferred embodiment the valve is a globe valve.

Preferably the middle water sprayer and the lateral water sprayers are tubes which are mounted to the conduit in a direction so that the tubes can be oriented in a downward direction when the tubes are positioned in the water shield for the washing operation. The tubes preferably have a plurality of orifices alongside portions thereof for spraying water onto the interior and exterior portions of the pouch.

With respect to the pouch, any conventional pouch can be used in this invention. Typically the pouch which is cleaned with this invention is a conventional colostomy pouch.

Figure 1:
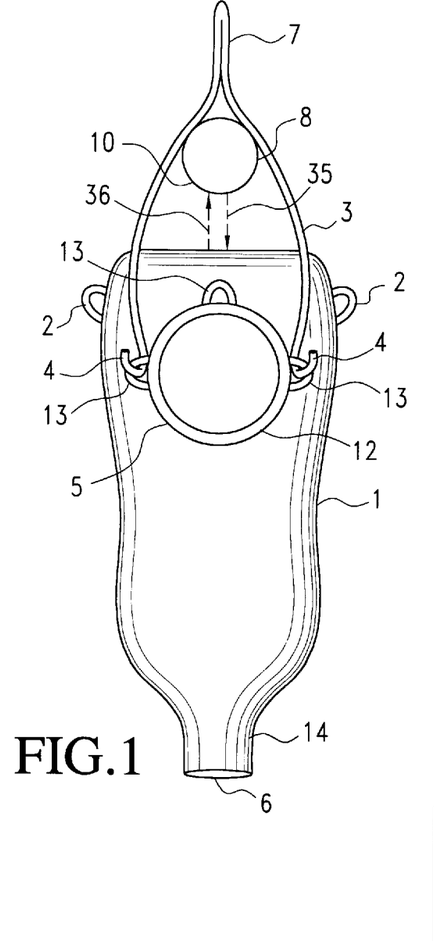
FIG. 1 is a perspective view of a colostomy pouch held in place by a holder which is used in the device of the present invention.

FIG. 1 illustrates a colostomy pouch 1 which includes a side opening 5 which is used for connecting the pouch to the stoma. Typical colostomy pouches include a ring 12 around the side opening 5 with apertured ears 13 extending from the ring. The apertured ears 13 are provided to allow the user to vent excessive gas in the pouch by tugging on the ears when it is necessary to do so. In the present invention the ears may serve as connectors for attaching the holder 3 to the pouch. Holder 3 is preferably a hanger made out of wire such as copper wire and preferably includes hooked terminal portions 4 for grasping apertured ears 13. If the pouch does not include a ring with apertured ears 13, then other suitable connecting devices may be used. For example, the pouch may be modified by including connectors 2 at any appropriate location so that the hooked terminal portions 4 of the holder can be connected thereto. While the above described ears and connectors 2 are suitable for facilitating the connection between hanger 3 and pouch 1, it will be appreciated by one skilled in the art that any suitable connection device can be used.

Typical conventional pouches include a bottom opening 6 which is provided on a bottom narrow portion 14 of the pouch for elimination of accumulated waste contained in the pouch. When the pouch is being worn by a patient, a clip is attached to the narrow portion 14 to keep opening 6 closed. This clip is readily removed from the pouch so that the pouch can be cleaned in accordance with this invention.

The holder 3 is preferably configured to form a top handle 7 so that the holder can be held by the person cleaning the pouch without having to touch the pouch.

Figure 5:
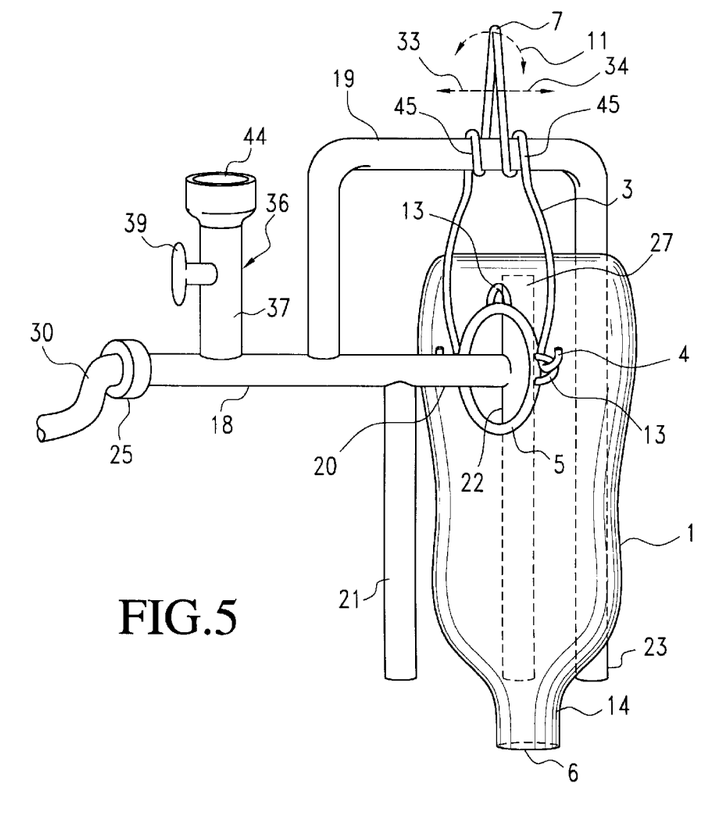
FIG. 5 is a perspective view of the present invention which illustrates the position of the bag which is cleaned by the claimed device.

The holder 3 may be configured to rest on support 8. In a preferred embodiment support 8 comprises a portion of the conduit and the holder is a wire hanger attached to the support by a portion 45 of the wire being wrapped around the support as shown in FIG. 5.

It is also possible to configure the holder 3 so that when the holder 3 rests on support 8, the top 9 of pouch 1 can be raised upward to the bottom portion 10 of support 8 and then lowered back down to the starting position. This upward and down motion is shown by dashed arrows 35 and 36. The aforementioned upward and downward movement of the bag facilitates cleaning of the bag during the washing procedure.

Figure 2:
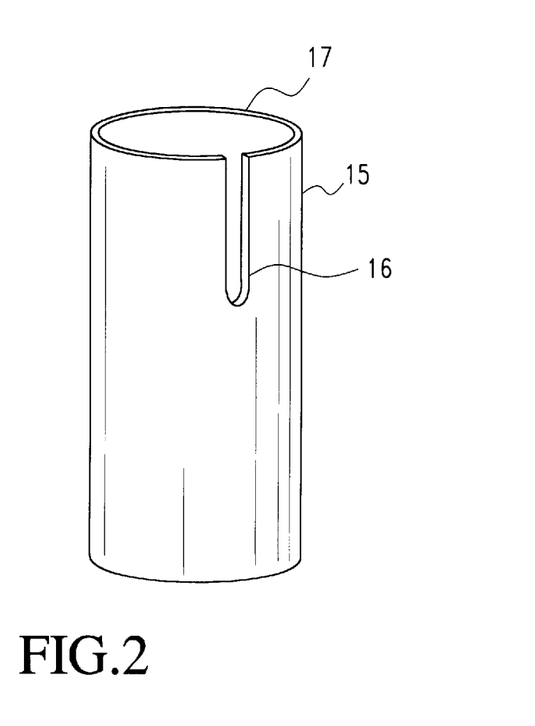
FIG. 2 is a perspective view of a water shield used in the device of the present invention.

The splash shield is preferably a plastic cylinder 15 illustrated in FIG. 2. The cylindrical plastic cylinder advantageously includes a slot 16 extending downward from top 17 to facilitate insertion of the water sprayers within the cylindrical water shield. In a preferred embodiment the shield is a cylinder about 16 inches long and about 8 inches wide with a 5" slot extending downward from the top.

Figure 3:
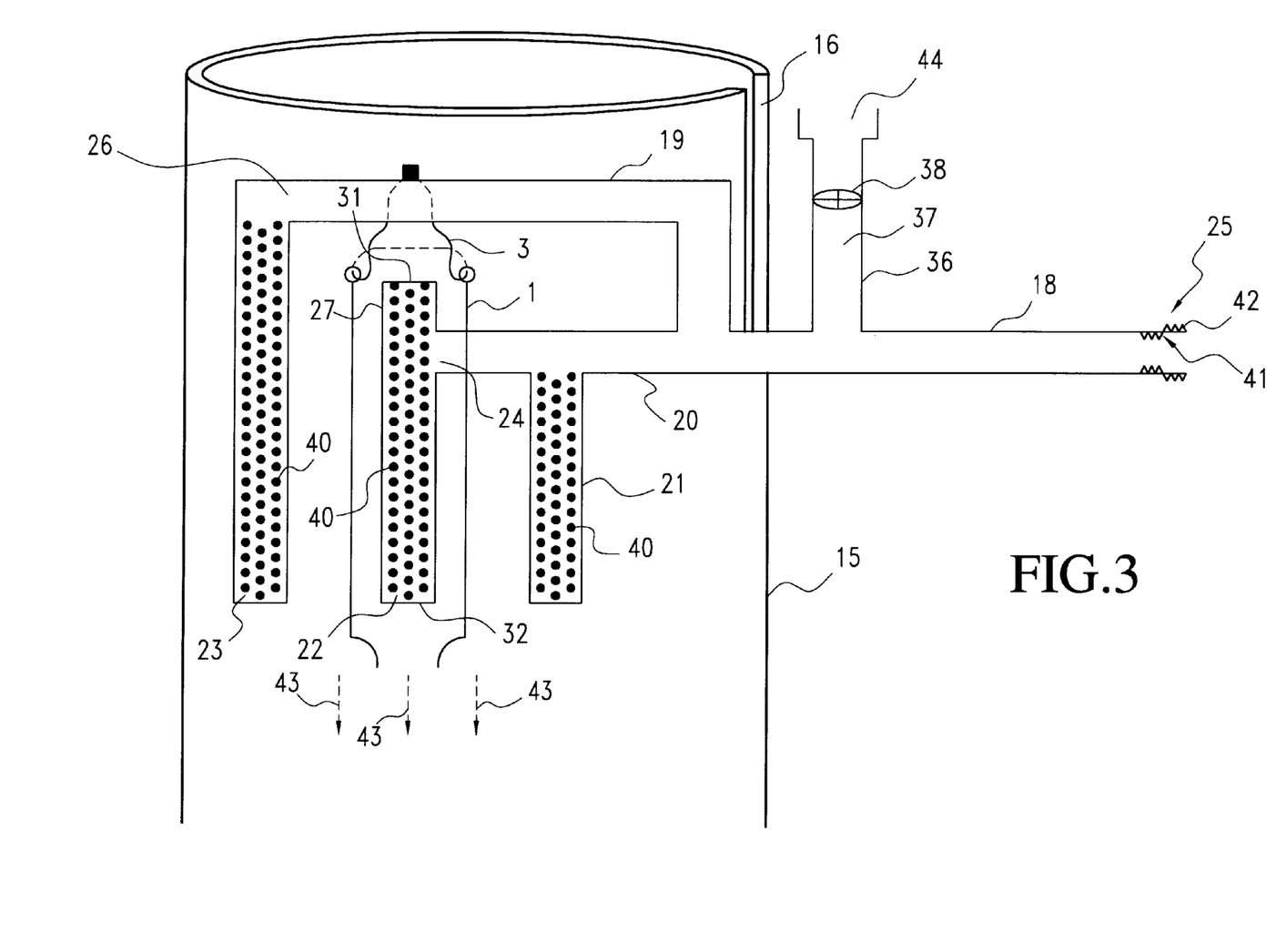
FIG. 3 is a partial cross-sectional view of an embodiment of the present invention.

FIG. 3 illustrates a preferred configuration of the conduit, the middle water sprayer and the two lateral water sprayers. More particularly, the conduit 18 is preferably bifurcated to form a first branch (i.e., a bottom branch) 20 and a second branch (a top branch) 19. The middle water sprayer 22 is connected to terminal portion 24 of first branch 20. A first lateral water sprayer 21 is connected to the first branch 20 between the middle water sprayer 22 and coupler 25. A second lateral water sprayer 23 is connected to terminal portion 26 of the second branch 19.

In one embodiment of the invention the portion of conduit 18 which is adjacent to coupler 25 may be an elongated flexible hose. In such an embodiment the coupler 25 may be adapted to connect directly with a faucet for supplying water to the device. In another embodiment the source of water is a flexible hose attached to a faucet and coupler 25 is adapted to connect to the flexible hose so that water passes from the faucet through the hose into the conduit 18.

Figure 4:
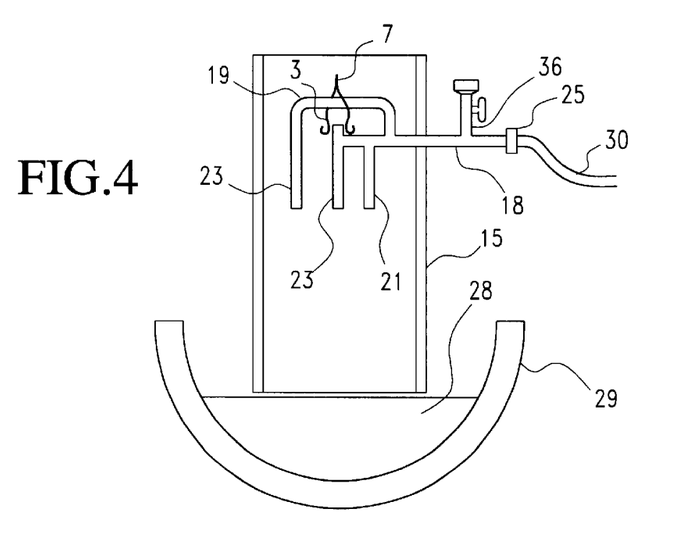
FIG. 4 is a cross-sectional view of an embodiment of the present invention being used in its intended environment.

In use the device shown in FIG. 3 is conveniently inserted into water shield 15 through slot 16. The water sprayers 21, 22 and 23 are connected to the conduit so that when the water sprayers are contained within water shield 15, they are oriented in a downward direction toward the water 28 in toilet bowl 29 as shown in FIG. 4. FIG. 4 also shows flexible hose 30 attached to conduit 80. During the cleaning operation, the middle sprayer 22 shown in FIG. 4 will be within the pouch.

It will be appreciated that when the device of the present invention is connected to a source of pressurized water, water will flow through coupler 25 and will flow through the conduit in a direction shown by arrow 46 (FIG. 7) toward sprayers 21, 22 and 23. Thus, it is self-evident that the conduit includes an upstream portion beginning at coupler 25 and a downstream portion ending at terminal portions 24 and 26.

The second branch 19 of the conduit lies above middle sprayer 22 when the device shown in FIG. 3 is oriented in water shield 15 as illustrated in FIG. 4. Thus, upper branch 19 may serve as a support for holder 3. In this embodiment upper branch 19 serves as support 8 shown in FIG. 1. In other words support 8 may be substituted by upper branch 19 for supporting holder 3. Holder 3 is preferably slidable along branch 19 so that the pouch can be moved upward and downward as previously described and also in a back and forth lateral motion to facilitate cleaning during the washing procedure. Alternatively, the holder 3 may be attached to branch 19 by any conventional connection device. For example the wire of holder 19 may be wrapped around branch 19 to effect the desired connection as illustrated in FIG. 5.

The sprayers 21, 22 and 23 are preferably tubes which have a plurality of openings or orifices which extend along the length of the tubes whereby water sprays at least a major portion of the pouch when the pouch is held around the middle water sprayer 22 between lateral water sprayers 21 and 23. However, it is preferable that the configuration of the tubes and the location of the orifices are such that the water spray cleans the entire pouch with minimal movement of the pouch being required during the washing procedure.

In a preferred embodiment middle sprayer 22 is attached to first branch 20 between an upper end 31 and a lower end 32 of middle sprayer 22 to thereby define an upwardly projecting portion 27 of middle sprayer 22. Projection 27 extends upward from branch 20. Preferably the length of projection 27 is selected so that a portion of middle sprayer 22 extends into the interior portion of pouch 21 above side opening 5.

Middle sprayer 32 lies between the two lateral sprayers 21 and 23. However, it is to be noted that it is not essential for middle sprayer 22 to be exactly centered between the two lateral sprayers. It is only necessary to position sprayer 22 between sprayers 21 and 23 although it is preferred that middle sprayer 22 should be centrally located between the two lateral sprayers 21 and 23. In other words, the term "middle" is not intended to define a geometric central position between the two lateral sprayers.

FIG. 5 is a prospective view of the invention which shows pouch 1 with middle water sprayer 22 inserted therein. FIG. 5 also shows upper projection 27 extending into the portion of the pouch which lies above side opening 5. FIG. 5 also shows the aforementioned lateral motion which is made possible by holder 3 being in sliding engagement with second branch 19. The back and forth lateral motion is depicted by dashed arrows 33 and 34. Dashed arrows 11 in FIG. 5 depicts a rotational motion which is possible by rotating handle 7 back and forth around the conduit. This rotational movement, like the aforementioned lateral movement, facilitates the cleaning process.

The dispenser 36 preferably comprises a tube 37 which extends upward from conduit 18 so that liquid soap or detergent can be dispensed by gravity flow into the conduit. The tube 37 includes a valve 38 which is preferably a globe valve. The valve is open so that liquid soap or detergent can be dropped into the tube through an enlarged upper opening 44. Once the soap has been introduced through the tube 37, the valve 38 is then closed so that pressurized water cannot escape therethrough during the cleaning operation. The valve is actuated by a handle 39 which is mounted outside of the tube 37. The enlarged open top end 44 of tube 37 functions as a funnel and thereby facilitates pouring of liquid detergent or soap into the tube.

Figure 6:
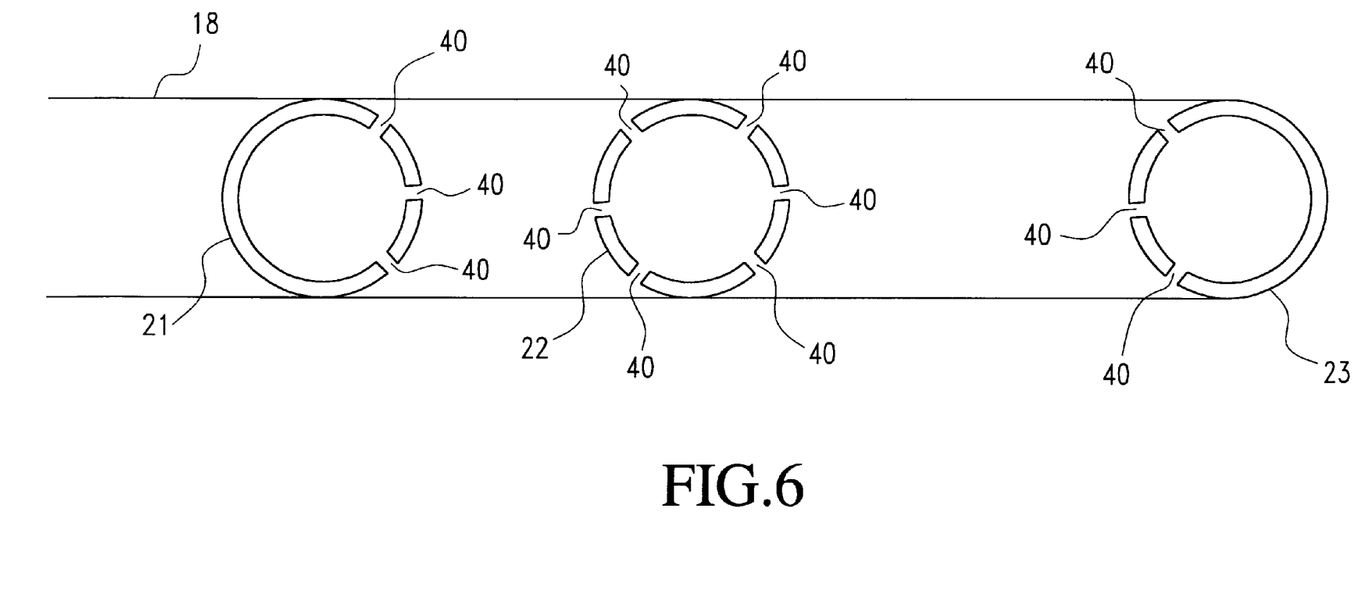
FIG. 6 is a cross-sectional view through the water sprayers used in the present invention.

FIG. 3 illustrates the device of the invention which includes sprayers 21, 22 and 23 located inside a cylindrical plastic well which serves as the water shield 15. Slot 16 is provided to facilitate insertion of sprayers 21, 22 and 23 within the water shield along with a portion of conduit 18 including branches 19 and 20. The sprayers 21, 22 and 23 are preferably tubes and include orifices 40 extending from the top to the bottom thereof. Water which reaches the sprayers sprays outward from openings 40 to provide washing action. The terminal portion of the sprayer tubes remote from the conduit are capped so that the water entering the tubes is forced out through the openings 40 to create the desired spray. Preferably the openings 40 extend around the circumference of middle sprayer 22 as shown in FIG. 6. The openings 40 in middle sprayer 22 shown in FIG. 6 will spray outwardly along the cross-sectional circumference of sprayer 40 to provide effective cleansing of the interior of the pouch when the pouch is placed around sprayer 22 as illustrated in FIGS. 3 and 5.

The openings in the two lateral sprayers 21 and 23 are preferably located only on a portion of the tubes so that the spray from lateral sprayers 21 and 23 only sprays in a direction toward the pouch around middle sprayer 22. For example, the openings 40 in lateral sprayers 21 and 23 are only on the side facing the middle sprayer 22. The coupler 25 illustrated in FIG. 3 may include a conventional threaded portion for attachment to a standard hose. For example, the coupler 25 may comprise a standard male hose adapter 41 with external male threads 42 for connecting to a corresponding threaded female terminal portion of a hose.

During the cleaning operation water from the sprayers will contact the interior and exterior or pouch 1 which hangs from holder 3. During the spraying operation the water will flow from the interior and exterior portions of the pouch in a downward direction illustrated by arrows 43 in FIG. 3. Since the lower end of the spray shield will be inserted into a conventional toilet bowl during the cleaning operation, the water along with the waste contained therein from the cleaning process will be directed into the water of the toilet bowl without any splashing and without any spray contacting the operator during the cleaning procedure. Thus, the device operates in a sanitary manner for cleaning the pouch.

The conduit, the sprayers and the dispenser may be made of pipes such as metal or plastic pipe used in plumbing. Conventional connecting members which are used to connect metal or plastic pipes together may be used to assemble the various parts which are connected to the conduit. All of the parts which are used to assemble the components of this device which receive water under pressure should withstand 100 PSI at 180° F. and 400 PSI at 73° F. Preferably the conduit, dispenser tube and the tubes of the sprayer should have a ½" inside diameter.

The spray shield is preferably made from plastic material such as PVC, polyethylene, polypropylene, or similar material. The material of the spray shield should be of sufficient thickness so that the spray shield has a self sustaining shape.

Figure 7:
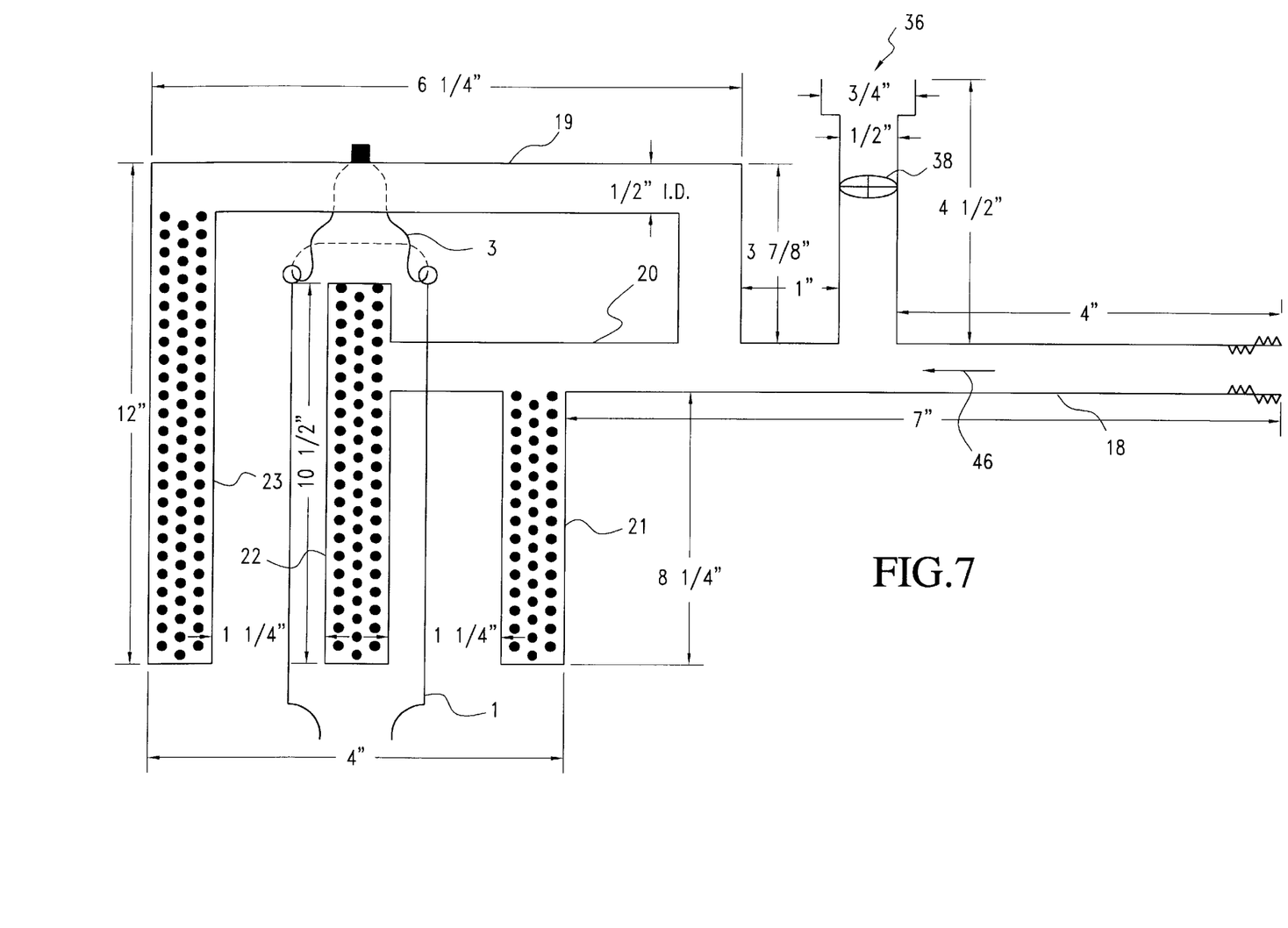
FIG. 7 is a partial cross-sectional view of an embodiment of the present invention shown without a spray shield.

FIG. 3 illustrates a preferred embodiment of the invention wherein the dimensions are as indicated in FIG. 7 to maximize the performance of the device with currently available colostomy pouches.

The device shown in FIG. 7 includes middle water sprayer 22 wherein the openings or orifices through which the water sprays are arranged in 6 rows which extend the length thereof. The rows are about ¼" apart from each other. The orifices of each row are about 1/32" in diameter and are about ⅜" apart. The orifices of each row are arranged so that they are staggered in relationship to the orifices of adjacent rows.

The orifices of the lateral water sprayers are preferably arranged in three rows which extend along the length thereof about ¼" apart and the orifices of each row are about 1/32" in diameter and are about 1" apart from each other. The orifices of the lateral water sprayers shown in FIG. 7 are arranged so that the orifices of each row are in staggered relationship to the orifices of adjacent rows.

The device described herein is conveniently used to clean human waste from a bag or pouch designed to collect human waste through a surgically created opening in a human body. In operation the pouch is positioned around the middle water sprayer and attached to the holder so that the pouch remains in position during the cleaning operation. The sprayers are inserted into the spray shield with the pouch positioned around the middle water sprayer. The sprayers are inserted into the water shield preferably by inserting at least the portion of the conduit to which the sprayers are attached, through the slot of the cylindrical water shield. The coupler is attached to a source of water which is preferably a flexible hose which in turn is connected to a faucet. Prior to the introduction of water into the device, soap or detergent is added to the conduit through the dispenser. If the dispenser includes a valve as shown in a preferred embodiment of the invention, the valve is closed after the introduction of soap or detergent so that water under pressure does not escape through the dispenser during the washing procedure. Also, before the device is used to spray water onto the pouch, the bottom portion of the spray shield is positioned in the toilet bowl so that water from the spray along with waste can be discharged into the toilet through the lower end of the spray shield. Preferably warm water is used.

Cleaning takes place as water flows through the conduit and sprays through sprayers 21, 22 and 23 simultaneously to thereby simultaneously clean the interior and exterior of the pouch.

During the cleaning procedure, the pouch may be moved or jiggled somewhat by moving holder 3 laterally along branch 19 of the conduit. In addition, the pouch may be moved somewhat during the cleaning procedure by slightly rotating holder 3 around branch 19 in a slight back and forth manner. The above-described lateral and back and forth rotational motion helps the spray contact all areas of the pouch during the cleaning operation. Of course, the above-described motion should not be so severe so as to cause the pouch from being removed from the sprayer during the spraying procedure.

The cleaning procedure takes only a few minutes. Once the pouch has been adequately cleaned, the flow of water may then be stopped so that the sprayers along with the pouch can be removed from the spray shield either before or after the spray shield is removed from the toilet. Care should be taken to continue the flow of water so that all fecal material is removed from the pouch and the spray shield before the spray shield is removed from the toilet bowl.

Once the cleaning operation is finished, the pouch is conveniently removed from the middle sprayer. The pouch may be dried and immediately reused or saved for later use. The waste removed from the pouch is conveniently disposed by flushing the toilet.

While the present invention has been described in terms of certain preferred embodiments, one skilled in the art will readily appreciate that various modifications, changes, omissions and substitutions may be made without departing from the spirit thereof. It is intended, therefore, that the present invention be limited solely by the scope of the following claims.

I claim:

1. A device for washing a colostomy pouch which comprises:

a middle water sprayer configured for receiving said pouch around said middle water sprayer so that said middle water sprayer extends inside said pouch for cleaning the interior of said pouch with sprayed water;

at least two lateral water sprayers located alongside said middle water sprayer, said lateral water sprayers being configured to clean the exterior of said pouch when said middle water sprayer extends inside said pouch;

a holder configured for holding said pouch at a location wherein said middle sprayer is extended within said pouch for interior cleaning thereof and said lateral water sprayers are disposed alongside the exterior of said pouch for exterior cleaning thereof;

a conduit for passing water therethrough, said middle water sprayer and said lateral water sprayers being connected to said conduit, said conduit being in fluid communication with said middle water sprayer and said lateral water sprayers so that water flowing through said conduit enters said middle water sprayer and said lateral water sprayers to be sprayed therefrom;

a coupler connected to said conduit for connecting said conduit to a source of water under pressure so that the water can flow through said conduit toward said middle water sprayer and said lateral water sprayers for the supply of water thereto;

a spray shield having an upper end configured to contain said middle water sprayer and said lateral water sprayers therein and a lower end configured to fit in a toilet bowl so that water sprayed from said middle water sprayer and said lateral water sprayers and material cleaned from said pouch are directed to said toilet bowl for disposal.

2. The device of claim 1 which further includes a dispenser connected to said conduit, said dispenser being configured for dispensing cleaning agent, sanitizing agent, deodorizing agent or combination thereof into said conduit so that said cleaning agent, sanitizing agent or deodorizing agent can mix with said water to thereby aid in cleaning, sanitizing or deodorizing of said pouch.

3. The device of claim 2 wherein said dispenser comprises a tube having a lower end in fluid communication with said conduit and an upper end for the introduction of soap or detergent therein; said tube including a valve between said upper and lower ends wherein said valve is configured so that it can be opened to allow passage of said soap or detergent through said dispenser into said conduit by gravity and so that said valve can be closed to prevent leakage of water when said water enters said device under pressure.

4. The device of claim 3 wherein said valve is a globe valve.

5. The device of claim 4 wherein said middle water sprayer and said lateral water sprayers are tubes which are mounted to said conduit in a direction so that said tubes can be oriented in a downward direction when said tubes are contained in said water shield; and said tubes have a plurality of orifices alongside portions thereof for spraying water onto said pouch.

6. The device of claim 5 wherein the number of lateral water sprayers is 2 which are first and second lateral water sprayers.

7. The device of claim 6 wherein the tube of said middle water sprayer and the tubes of said lateral water sprayers have orifices which extend along a length of said tubes whereby water spray sprays at least a major portion of said pouch when said pouch is held around said middle water sprayer between said lateral water sprayers.

8. The device of claim 7 wherein said tubes are configured and the number and location of said orifices of said tubes are selected so that said water spray cleans the entire pouch.

9. The device of claim 7 wherein the orifices of said lateral water sprayers are located only on a half portion of said lateral water sprayers facing said middle water sprayer.

10. The device of claim 9 wherein said spray shield is in the form of a cylinder.

11. The device of claim 10 wherein said cylinder has a slot in said upper end thereof for the introduction of said middle water sprayer and said lateral water sprayers therein.

12. The device of claim 11 wherein said holder is a hanger configured to connect to said pouch for hanging said pouch from said hanger around said middle water sprayer;

said conduit is bifurcated to define a first branch of said conduit and a second branch of said conduit, said middle water sprayer being connected to a terminal portion of said first branch, said first lateral water sprayer being connected to said first branch between said middle water sprayer and said coupler, and said second lateral water sprayer being connected to a terminal portion of said second branch;

said hanger is configured to hang said pouch at a location whereby said terminal portion of said first branch extends through an opening in a side portion of said pouch; and said middle water sprayer is connected to the terminal portion of said first branch between an upper end of said middle water sprayer and a lower end of said middle water sprayer to thereby create a portion of said middle water sprayer which extends above said conduit and a portion of said middle water sprayer extending below said conduit.

13. The device of claim 12 wherein said hanger is a wire hanger.

14. The device of claim 13 wherein said hanger is attached to said device.

15. The device of claim 13 which includes a support member over said middle water sprayer for supporting said hanger over said middle water sprayer and said hanger is in sliding engagement with said support member.

16. The device of claim 15 wherein said support member comprises a portion of said second branch of the conduit which extends over said middle water sprayer.

17. The device of claim 16 wherein said source of water is a flexible hose connected to a faucet and said coupler is configured for attachment to said hose; or said source of water is a faucet and a portion of said conduit connected to said coupler is a flexible hose.

18. The device of claim 17 wherein said source of water is a flexible hose connected to a faucet and said coupler includes a union and male hose adapter for connection to said hose.

19. The device of claim 18 wherein said orifices of said middle water sprayer are arranged in 6 rows which extend along the length thereof, said rows being about ¼" apart from each other; said orifices of each row being about 1/32" in diameter and about ⅜" apart; and the orifices of each row are arranged so that the orifices of each row are staggered in relationship to the orifices of adjacent rows; and said orifices of said lateral water sprayers are arranged in 3 rows which extend along the length thereof about ¼" apart and the orifices of each row are about 1/32" in diameter and are about 1" apart from each other and the orifices of each row are arranged so that the orifices of each row are in staggered relationship to the orifices of adjacent rows.

20. A method for cleaning human waste from a bag or pouch designed to collect said waste through a surgically created orifice in a human body, said method comprising:

placing said bag or pouch in a spray shield;

inserting a lower end of said spray shield into a toilet;

spraying the interior and exterior of said pouch or bag in said spray shield with an aqueous cleaning liquid, said spraying being carried out by using a sprayer located in an interior portion of said bag for spraying the interior of the bag or pouch and using at least 2 sprayers located exteriorly to said bag or pouch for spraying the exterior of said bag or pouch whereby said spraying removes said waste from said bag or pouch;

draining said water and said waste removed from said bag or pouch through an opening in said bag or pouch; and passing said water and said waste removed from said bag through an opening located in said lower end of the spray shield inserted into the toilet so that said water and said waste may be disposed of by flushing said toilet.

21. The method of claim 20 wherein said aqueous cleaning liquid contains a cleaning agent, a sanitizing agent, a deodorizing agent or combination thereof.

22. A method for cleaning a bag or pouch used to collect waste from a surgically created body opening which comprises using the device of claim 2 wherein said bag or pouch is placed around said middle water sprayer;

soap or detergent is added to said conduit through said dispenser;

said coupler is attached to a source of water under pressure;

said lower end of said spray shield is inserted into a toilet bowl;

said middle water sprayer with said bag or pouch placed around said middle water sprayer and said lateral water sprayers are positioned in said water shield;

water is flowed through said conduit containing said soap or detergent and is sprayed with said soap or detergent onto said bag or pouch through said middle water sprayer and said lateral water sprayers whereby said waste is removed from said bag or pouch by said water;

said water and said waste are then discharged into said toilet through the lower end of said spray shield.

* * * * *